US00PP20444P2

(12) United States Plant Patent
Utecht

(10) Patent No.: US PP20,444 P2
(45) Date of Patent: Oct. 27, 2009

(54) ***PELARGONIUM* PLANT NAMED 'FISTAN'**

(50) Latin Name: *Pelargonium×hortorum*
Varietal Denomination: Fistan

(75) Inventor: Angelika Utecht, Montabaur (DE)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 12/228,481

(22) Filed: Aug. 13, 2008

(51) Int. Cl.
*A01H 5/00* (2006.01)

(52) U.S. Cl. ..... Plt./330

(58) Field of Classification Search ..... Plt./330
See application file for complete search history.

(56) References Cited

OTHER PUBLICATIONS

Upov Plant Variety Database 2009/02 p. 1.*

* cited by examiner

*Primary Examiner*—Annette H Para
(74) *Attorney, Agent, or Firm*—S. Matthew Edwards

(57) ABSTRACT

A new *Pelargonium* plant named 'Fistan,' particularly distinguished by the medium sized, brilliant scarlet-red, semi-double flowers, large inflorescences with reddish peduncles, dark-green leaves with strong zonation, medium to large sized, mounding habit, and early to medium beginning of flowering.

1 Drawing Sheet

Latin name of the genus and species of the plant claimed: *Pelargonium×hortorum.*

Varietal denomination: 'Fistan'.

BACKGROUND OF THE NEW PLANT

The present invention comprises a new *Pelargonium,* botanically known as *Pelargonium×hortorum* and hereinafter referred to by the variety name 'Fistan.'

'Fistan' is a product of a planned breeding program. The new cultivar has scarlet-red flower color, large inflorescences, reddish peduncles, dark-green foliage with strong zonation, good branching ability for a dark green leaved variety, medium or oversized, mounding plant habit, and early to medium begin of flowering.

'Fistan' originated from a hybridization made in the summer of 2003 in a controlled breeding program in Hillscheid, Germany. The female parent was the commercial variety 'Fistafire,' U.S. Plant Pat. No. 16,641, with large flowers, orange-red flower color, large inflorescences, dark green foliage with narrow leaf zone, and relatively tall plant habit.

The male parent of 'Fistan' was an unpatented hybrid seedling identified as 'k94-2063-1' with red, semi-double-type flowers, and dark green foliage.

'Fistan' was selected as one flowering plant within the progeny of the stated cross in the spring of 2004 in a controlled environment in Galdar, Gran Canaria, Spain.

The first act of asexual reproduction of 'Fistan' was accomplished when vegetative cuttings were taken from the initial selection in the fall of 2004 in a controlled environment in Galdar, Gran Canaria, Spain.

Horticultural examination of plants grown from cuttings of the plant initiated in March 2005 in Hillscheid, Germany, and continuing thereafter, has demonstrated that the combination of characteristics as herein disclosed for 'Fistan' are firmly fixed and are retained through successive generations of asexual reproduction.

'Fistan' has not been observed under all possible environmental conditions. The phenotype may vary significantly with variations in environment such as temperature, light intensity and day length.

Plant Breeder's Rights for this cultivar was applied for in Germany on Feb. 21, 2007 and in Canada on Mar. 30, 2007. 'Fistan' has not been made publicly available more than one year prior to the filing of this application.

DESCRIPTION OF THE DRAWING

This new *Pelargonium* plant is illustrated by the accompanying photographic drawing which shows blooms, buds, and foliage of the plant in full color. The colors shown are as true as can be reasonably obtained by conventional photographic procedures. The photographic drawing shows a flowering potted plant of the new variety.

DETAILED BOTANICAL DESCRIPTION

The measurements were taken in Hillscheid, Germany, in mid May 2007 (10 week old) plants that were growing in a greenhouse. Culture of these plants had started in early March when rooted cuttings were potted into 12 cm pots, and were grown out, unpinched, at an average day/night temperature of (only) 14° C. until mid of April, and at higher temperature thereafter.

Color Chart used: Royal Horticultural Society Colour Chart (R.H.S.) 2001.

BRIEF SUMMARY OF INVENTION

The following observations, measurements, and comparisons describe plants grown indoors and outside in Hillscheid/Germany, and in Chatellerault, France. The following traits have been repeatedly observed and are determined to be basic characteristics of the new variety. The combination of these characteristics distinguishes this *Pelargonium* as a new and distinct variety:

1. Brilliant scarlet flower color
2. Round, semi-double flower shape
3. Large umbels, borne well above the foliage canopy
4. Dark green foliage with relatively strong zonation
5. Medium to over in size, mounding and well-branched plant habit for a dark leaved variety
6. Early to medium spring flowering response.

TABLE 1

DIFFERENCES BETWEEN THE NEW VARIETY 'FISTAN' AND SIMILAR VARIETIES

| | 'Gravio' | 'Tango' (U.S. Plant Pat. No. 5,933, no longer in force) |
|---|---|---|
| Flower color | More brilliant, scarlet red | Medium red color |
| Leaf color and zonation | Slightly deeper green with zone of medium to strong distinctness | Deep green with no or only very weak zone |
| Color of peduncles | Mainly purple/reddish-brown | Mostly green |
| | 'Gravio' | 'Fistafire' (U.S. Plant Pat. No. 16,641) |
| Flower color | Somewhat closer to red, RHS 44A to 44B | More orange hue, RHS N30A mainly |
| Flower shape, size | Medium size, weak cup-shape | Larger, wider open shape with fewer inner petals |
| Foliage, zone | Strong | Somewhat less distinct, narrower |
| | 'Fistan' | 'Fishimred' (U.S. Plant Pat. No. 16,650) |
| Leaf zone | Relatively strong | (Very) weak |
| Inflorescences borne | Medium height above the foliage | Higher above the foliage, long peduncles |
| Plant size | Medium to tall, lower, mounding habit | Taller, more spreading habit |
| | 'Fistan' | 'Fisboogy' (U.S. Plant Pat. No. 9,774) |
| Plant size | 13.9/25.3 cm | 12.5/21.6 cm |
| Umbel diameter | 12.0 cm | 9.4 cm |
| Foliage color | Dark green with strong zonation | Appears somewhat less deep green, nearly no zonation |

Plant:

*Form, growth and habit.*—Shrub, self-branching, relatively well branching, mounding plant habit with the flower heads well, but not too high above the foliage.

*Plant height (foliage).*—13.9 cm.

*Plant height (inflorescence included).*—23.5 cm.

*Plant width.*—25.3 cm.

*Plant size at the end of the summer.*—32 cm (6 months old, on August 28).

*Plant width at the end of the summer.*—About 30 cm in diameter.

Stem:

*Number of branches.*—6.3.

*Color of stem.*—Partly green, RHS 143C, partly brown, RHS 178A or weaker.

*Length of stem.*—About 12–18 cm.

*Diameter.*—0.9–1.1 cm (at mid portion).

*Length of internodes.*—1–3 cm.

*Texture.*—Dense pubescence.

Foliage:

*Immature, leaf color, upper surface.*—RHS 137A to 137B Lower surface: intermediate between RHS 138A and 143C.

*Mature, leaf color, upper surface.*—RHS 137A Lower surface: intermediate between 138A and 143B.

*Length.*—8.6 cm.

*Width.*—5.5 cm.

*Shape.*—Kidney-shaped to nearly round.

*Base shape.*—Cordate with a gap between lowest lobes.

*Apex shape.*—Rounded.

*Margin.*—Bi-crenate.

*Texture.*—Velvety, densely covered with very short hair, both surfaces.

*Color of zone.*—Dark brown, RHS 200B.

*Color of veins, upper surface.*—Indistinct, RHS 143A.

*Color of veins, lower surface.*—143C to 144C.

*Petiole color.*—RHS 143B to 143C.

*Petiole length.*—About 5.5 to 8 cm.

*Diameter of petiole.*—3 mm.

*Texture.*—Dense short hair.

Inflorescence:

*Type.*—An umbel, semi-spherically shaped Begin of flowering (50% of plants With at least one open flower): April 24 to May 1, about 8–9 week-old.

*Duration of flowering.*—Continuous flowering throughout the Summer.

*Number of inflorescences per plant.*—2–3; 7–8 in late summer.

*Number of flowers and buds per umbel.*—Approximately 50–75.

*Umbel diameter.*—12.0 cm.

*Umbel depth.*—5.5–6.0 cm.

*Numbers of flowers and buds per inflorescence.*—About 30 to 50.

*Color of peduncle.*—Partly green, RHS 144A or 146C; mainly purple-brown, RHS 178A to 183A.

*Length of peduncle.*—15.4 cm.

*Peduncle diameter.*—3–4 mm.

*Texture.*—Covered with glandular hair.

*Color of pedicel.*—Mainly reddish-brown, with intensity increasing from base to end: from RHS 146A to 174A and even 166A.

*Length of pedicel.*—2.5 cm on average.

*Diameter of pedicel.*—1.5 mm.

*Texture.*—Densely covered short hair, partly glandular hair.

Corolla:

*Form.*—Semi-double type, round, saucer-shape.

*Diameter of flower.*—4.3–4.5 cm.

*Depth of flower.*—About 1.5 cm.

*Number of petals.*—7–9.

*Color upper petals, upper surface.*—RHS 44A to 44B, no markings.

*Color upper petals, lower surface.*—RHS 43B or lighter, somewhat variable.

*Length of upper petals.*—21–23 mm.

*Width of upper petals.*—19–21 mm.

*Color lower petals, upper surface.*—RHS 44B, may turn RHS 45C.

*Color lower petals, lower surface.*—RHS 43B or lighter.

*Length of lower petals.*—20–22 mm.

*Width of lower petals.*—20–22 mm.

*Petal shape.*—Obovate.

*Apex shape.*—Rounded.

*Margin.*—Entire.
*Petal texture.*—Smooth, glabrous.
*Number of petaloids.*—1–3.
*Color petaloids.*—Red, RHS 44B upper side, RHS 43B for the lower side.

Bud (just before opening):
*Color.*—Orange-red, RHS 43A to 44A.
*Length.*—15 mm.
*Width.*—11 cm.
*Shape.*—Elliptical.

Calyx:
*Number of sepals.*—5.
*Color of sepals.*—Green, RHS 143B to 144A, base of largest sepal with anthocyanin at base: RHS 166A.
*Length of sepals.*—9–11 mm.
*Width of sepals.*—5 mm for the largest sepal, 3 mm for the other sepals.
*Sepal shape.*—Lanceolate.
*Apex shape.*—Acute.
*Margins.*—Entire.
*Texture.*—Covered with short glandular hair, and a few longer, soft hairs.

Reproductive organs:
*Pistil.*—One.
*Length.*—7 mm.
*Style color.*—Reddish, RHS 47C.
*Style length.*—3–4 mm.
*Stigma color.*—Reddish, RHS 43A.
*Number of anthers.*—5 to 7.
*Length of anthers.*—2–3 mm.
*Anther color.*—RHS 53D or 54A.
*Length filaments.*—7–8 mm.
*Color of filaments.*—Mainly white; (salmon) pink, RHS 50B at upper end.
*Pollen amount.*—Moderate/Typical for the species.
*Color of pollen.*—RHS 28B (orange).
*Fertility/seed set.*—Not observed.

Disease/pest resistance: Disease resistance and/or susceptibility has not been observed on this hybrid.

What is claimed is:

1. A new and distinct variety of *Pelargonium* plant named 'Fistan,' substantially as illustrated and described herein.

* * * * *

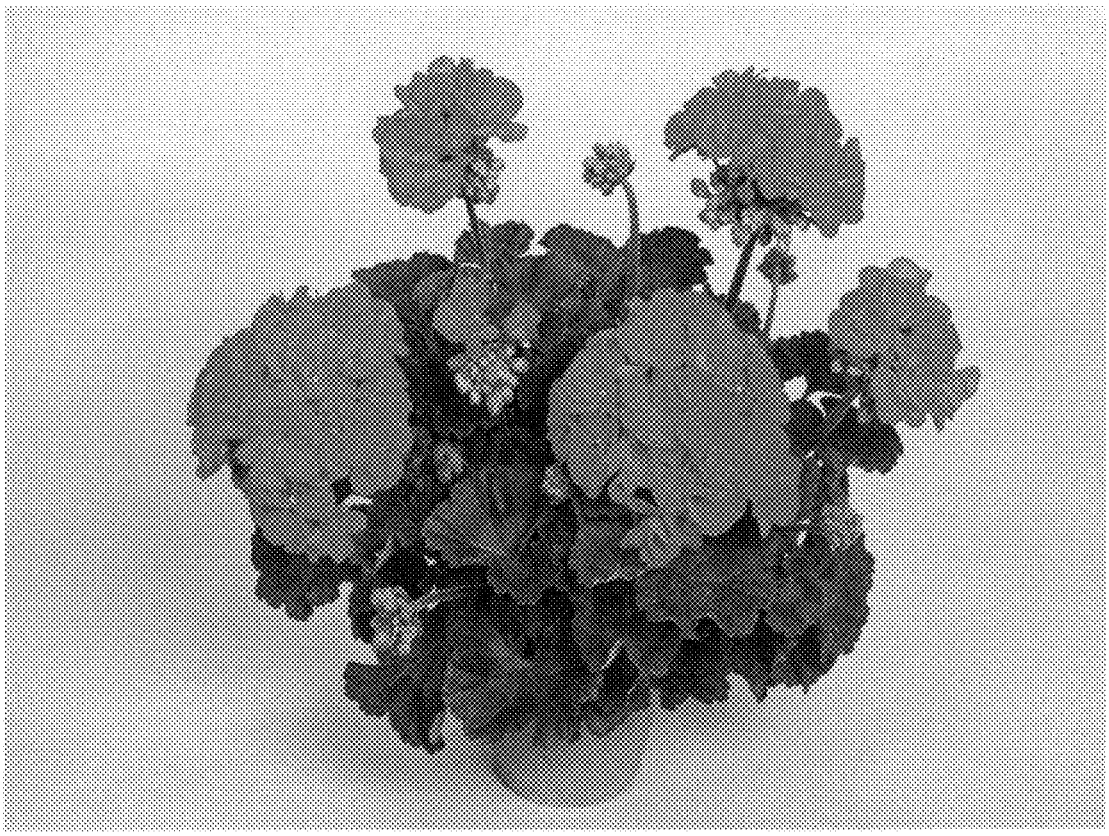

UNITED STATES PATENT AND TRADEMARK OFFICE

CERTIFICATE OF CORRECTION

PATENT NO. : PP 20,444 P2
APPLICATION NO. : 12/228481
DATED : October 27, 2009
INVENTOR(S) : Utecht It is certified that error appears in the above-identified patent and that said Letters Patent is hereby corrected as shown below:

At column 2, line 5, delete "was" before "applied" and insert therefor --were--

At column 3, line 15, in Table 1, delete "'Gravio'" and insert therefor --'Fistan'--

At column 3, line 32, in Table 1, delete "'Gravio'" and insert therefor ---'Fistan'--

At column 4, line 23, delete "Begin of" following "shaped"

At column 4, line 24, insert --Begin of-- in front of "flowering"

At column 4, line 24, delete "With" and insert therefor --with--

Signed and Sealed this

Fifteenth Day of December, 2009

David J. Kappos

David J. Kappos
*Director of the United States Patent and Trademark Office*